(12) United States Patent
Walter

(10) Patent No.: US 8,573,973 B2
(45) Date of Patent: Nov. 5, 2013

(54) DISPOSABLE ARTICULATOR HAVING AT LEAST ONE CONTINUOUS OPENING FOR ACCEPTANCE OF STABILIZATION MEANS

(76) Inventor: Jose Walter, Ranson, WV (US)

( * ) Notice: Subject to any disclaimer, the term of this patent is extended or adjusted under 35 U.S.C. 154(b) by 0 days.

(21) Appl. No.: 09/909,893

(22) Filed: Jul. 23, 2001

(65) Prior Publication Data

US 2002/0094505 A1 Jul. 18, 2002

Related U.S. Application Data

(60) Provisional application No. 60/220,149, filed on Jul. 24, 2000, provisional application No. 60/261,172, filed on Jan. 16, 2001, provisional application No. 60/270,146, filed on Feb. 22, 2001.

(51) Int. Cl.
*A61C 11/00* (2006.01)

(52) U.S. Cl.
USPC .............................................. 433/57

(58) Field of Classification Search
USPC ......... 433/57–68, 34–37, 74, 213, 47; 249/54
See application file for complete search history.

(56) References Cited

U.S. PATENT DOCUMENTS

| | | | | |
|---|---|---|---|---|
| 2,619,725 A | * | 12/1952 | Roeser | 433/60 |
| 4,200,981 A | * | 5/1980 | Fine | 433/60 |
| 4,283,173 A | * | 8/1981 | Browne et al. | 433/34 |
| 4,299,574 A | * | 11/1981 | Neihart | 433/213 |
| 4,508,506 A | * | 4/1985 | Jackson | 433/74 |
| 4,608,016 A | * | 8/1986 | Zeiser | 433/74 |
| 4,957,435 A | * | 9/1990 | Jinoian et al. | 433/34 |
| 5,506,095 A | * | 4/1996 | Callne | 433/34 |
| 5,622,497 A | * | 4/1997 | Cho | 433/60 |
| 5,658,143 A | * | 8/1997 | Kuperman | 433/60 |
| 5,788,489 A | * | 8/1998 | Huffman | 433/60 |
| 5,913,681 A | * | 6/1999 | Cho | 433/60 |
| 6,149,428 A | * | 11/2000 | Mogensen | 433/74 |

FOREIGN PATENT DOCUMENTS

WO   WO0004843   *   2/2000

* cited by examiner

*Primary Examiner* — Yogesh Patel

(57) ABSTRACT

An articulator has trays which have at least one opening with repeating broadened and narrowed regions allows for varying stabilization means to be used therewith. In one embodiment, the stone used for making the model acts as a stabilizing means without use of pins.

3 Claims, 4 Drawing Sheets

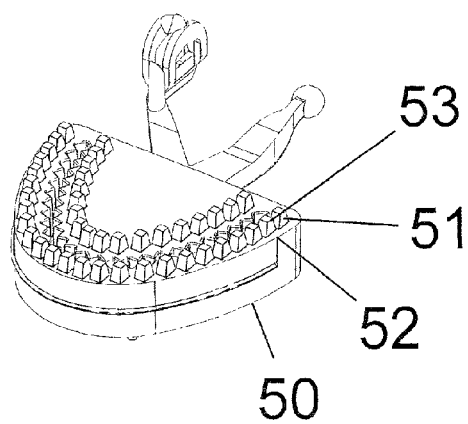
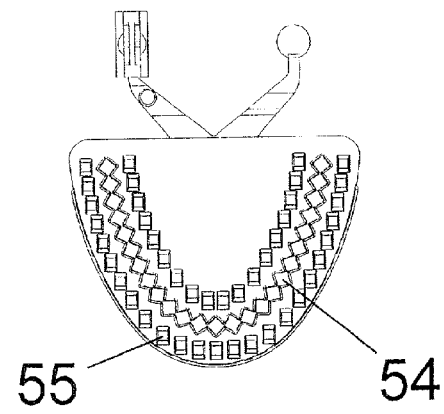
Fig. 12
Fig. 13
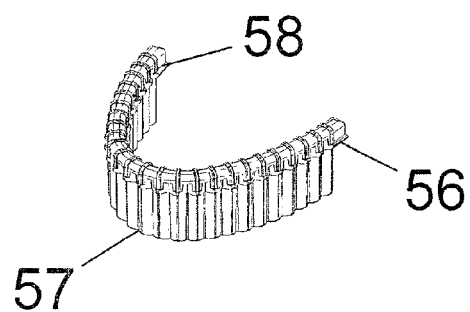
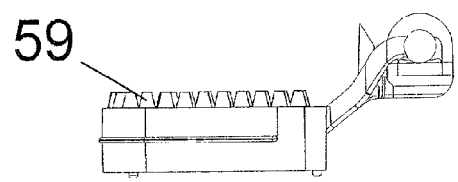
Fig. 14
Fig. 15

DISPOSABLE ARTICULATOR HAVING AT LEAST ONE CONTINUOUS OPENING FOR ACCEPTANCE OF STABILIZATION MEANS

This application claims priority from Provisional Application No. 60/220,149, filed Jul. 24, 2000, from Provisional Application No. 60/261,172, filed Jan. 16, 2001 and from Provisional Application No. 60/270,146 filed Feb. 22, 2001.

FIELD OF THE INVENTION

This invention relates to articulators, apparatus for making dental models for use in production of bridges, crowns, and other restorative articles.

BACKGROUND OF THE INVENTION

The production of restorative objects such as crowns, bridges and tooth prostheses requires use of dental models from which to work. Such models are created using a negative impression of the teeth. The negative impression is then filled with casting materials which harden, thus creating models of the patient's teeth. In order to work with these models, the casting material must be sawed into smaller pieces. It is essential to be able to realign the pieces in the appropriate manner.

In making of models, the technician uses a device known as an articulator, which is an instrument which simulates the movements of the mandible and aids in the construction of dental restorations.

The prior art includes several devices for use in making the models. U.S. Pat. No. 4,398,884 to Huffman, which describes an insert which locks onto the casting material to guide removal of model teeth during insertion into and withdrawal from the dental model presents an approach to the need to divide, then reassemble the models. However, the devices disclosed therein do not provide means for relating the maxillary and mandibular dental arches with one another in such a way as to create an accurate three-dimensional model showing the arches as they were at the time the impression was made.

Another apparatus for creating dental models is disclosed in U.S. Pat. No. 4,708,835, to Kiefer, wherein a base plate containing a plurality of pre-formed holes is fitted with dowel pins in each location where it is desired to make a die removable from a cast dental arch. Two methods of determining which of the pre-formed holes in a base plate are to have dowel pins inserted in them are disclosed. One version requires the use of a transparent datum plate which is positioned over the base plate and fitted with marker pins at desired locations. The data plate is then removed from the carrier plate, flipped over and remounted on the opposite side of the upright of the carrier plate. The base plate is then mounted to the upright of the carrier plate, over the data plate, and dowel pins are inserted into preformed holes in the base plate at those positions occupied by marker pins in the underlying data plate. Both datum plate and base plate with dowel pins inserted are then removed from the carrier plate, and the base plate is again flipped over and remounted to the opposite side of the carrier plate upright over a dental impression containing freshly poured liquid die stone, and pushed downward so the base plate contacts the impression.

U.S. Pat. No. 4,371,339 to Zeiser, requires the use of a complicated and expensive orienting apparatus which has been manufactured to precise tolerances for holding a dental impression while determining the locations on a prefabricated base plate where holes are subsequently to be made for securing dowel pins which will be molded into a dental arch.

Whelan, in U.S. Pat. No. 4,439,151, describes a method to facilitate the mounting and dismounting of individual teeth by use of a central plastic insert member having projecting elements through the base of the tray to facilitate removal by pushing on said projection portions. The devise also includes a means to pivot the trays apart to 180 degrees to provide filling of both tray and impressions. A shortcoming of this device is that a model of only the mandibular or maxillary arch can be made. The model must then be removed from one member of the device and inserted into the second member before work on the model can be accomplished.

U.S. Pat. No. 5,466,152 to Walter discloses and claims a dental articulator system containing a plurality of holes in the tray support into which pins are inserted before the casting material is placed into the tray. The pins provide indexing means for reassembly of the model after it has been divided into smaller pieces. The trays having multiple holes for insertion of indexing pins are more difficult to make than the trays of the instant invention. Furthermore, they do not allow for the broad discretion in placement of pins that is available when the reciprocating acceptor region is one continuous opening in the tray.

PCT Application PCT/US99/16508 of Walter discloses a tray support having an opening into which a protrusion from a tray is inserted. However, that disclosure does not teach use of a continuous opening that will accept pins, nor is the opening appropriate for use wherein stone is allowed to enter into the opening in the tray support. The use of that device requires that the model rest on the tray in the support. While the method of that disclosure provides a stable model, cutting through the tray requires very strong saws.

SUMMARY OF THE INVENTION

The instant invention provides an articulator having trays wherein said trays have at least one opening positioned through at least ½ of the length of the tray, said openings characterized by broadening and narrowing of said openings wherein said broadened areas (often referred to herein as receptor spaces) may be shaped to receive reciprocating indexing pins, or a part of a spine.

In another embodiment, the opening may be wider at the point where it opens to the superior surface of the tray. The wall of the opening taper so that the lower part of the opening is narrower. In the later instance, when the upper portion of the opening is sufficiently broad to accept stone readily, the bottom of the opening is sealed there may be no need for pins or a spine, since the stone forced into the opening will stabilize the model.

The shape of receptor spaces that accept pins or the portion of the spine to inserted into the opening may vary. However, in the preferred embodiments, the receptor areas are configured to receive pins which, in cross section, are not round, so that the pins will not rotate when inserted. In some instances, it is desirable to have two parallel continuous openings which can accept pins.

BRIEF DESCRIPTION OF THE FIGURES

FIG. 12 shows a tray for use in making full (bilateral) models of an entire jaw.

FIG. 13 shows a view of the tray for making a model of the entire jaw from above.

FIG. 14 shows a spine for use with the tray of FIG. 13.

FIG. 15 shows a lateral view of a tray with protrusions which provide stability to the models.

DETAILED DESCRIPTION OF THE INVENTION

Figure 1:
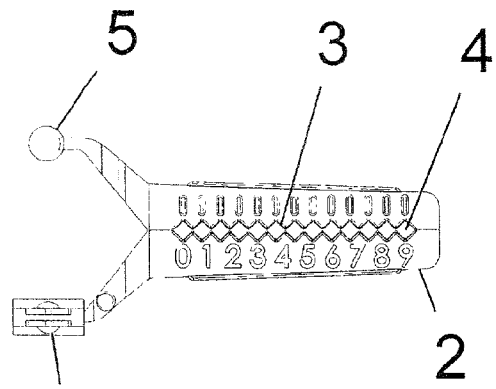
FIG. 1 is a top planar view of a tray for holding casting material such as plaster or stone, the tray being appropriate for making a model of teeth on one side of the jaw.

It is the purpose of this invention to provide an articulator which will be useful for making models for use in restorative dental work by providing a tray with at least one opening which, because of its shape, will allow for insertion of multiple reciprocating indexing pins or an insertion portion of a spine along the length of the opening or, if the receptor spaces are sufficiently broad at the superior surface of the tray and narrow toward the bottom of the opening, will accept sufficient stone to stabilize a model even without pins or a spine. The articulator of the invention is economical to produce and, if pins are used, provides for the possibility of replacing heat-susceptible pins in the original model with ceramic pins when the technician is making the final dental product. If pins are to be used, they may be placed in appropriate positions along the opening so that a part of a model of a particular tooth or group of teeth can be separated and worked on, then returned to the appropriate place on the tray.

In the practice of the invention two trays are assembled as mirrored parts connected with a hinge means. In the preferred embodiment, the two parts are interlocked with a hinge means which allows movement both laterally and horizontally during interaction with the impression or while evaluating and adjusting models.

The particular variations in shape of the broadened areas (receptor spaces) is not critical to practice of the invention, though the preferred embodiments wherein pins are used are so configured that they allow pins to fit in such a way that they can not be rotated. The pins and their reciprocal receptor spaces may be the same size/shape along the entire length of the tray or may vary. However, if pins are to be used, it is most economical to have the receptor spaces and pins the same shape and size along the entire length of the tray opening. The tray along with the pins and spine which fits in the opening may be sold as a unit to give the practitioner a choice of stabilizing elements.

Pins may be of any material which is sufficiently rigid and strong to resist distortion when casting material is applied to and worked on the tray. For usual purposes, metal or sufficiently strong and rigid plastic may be used for pins. When a ceramic prosthetic tooth is being made using the model, the pin as used in the model may be replaced by a ceramic pin which is the same configuration as the pin used in making the model from the impression. This allows the technician to fit the tooth into the tray containing the model of the teeth as produced on the articulator from the original casting.

The apparatus permits the user to make accurate models from impressions obtained by dentists doing restorative work. When fully assembled, the apparatus provides maxillary and mandibular tray members having the appropriate openings. In use, a negative dental impression may be filled with a casting material. The two halves of the articulator (the trays, wherein the two halves are made to interact by hinge means) are manipulated on said hinge means so that the tray on one half is pressed into the casting material in the mold formed by the negative dental impression. After the casting material has hardened, the opposing side of the negative impression is filled with casting material and the empty tray of the second half of the articulator is manipulated on the hinge means so that it presses into the casting material of the negative impression of the teeth of the other jaw. The entire articulator then has models of the maxillary and mandibular teeth on the trays. Alternatively, each tray with at least one pin in a receptor space may be loaded with casting material which is allowed to harden slightly. The casting material is formed into models by pressing said casting material into the appropriate impressions. Once the casting material has hardened sufficiently, the trays with the casting material are removed from the impression. When the casting material has fully hardened, the casting material with the indexing pins can be removed and dissected for further work. The tray with the models of the teeth may then be worked on as a unit or, as is more often the case, the models may be segmented to work on small portions, for example, the model of one tooth. Impressions of a model representing a tooth requiring replacement or reconstruction (hereinafter often referred to as the "target tooth") may be made, then a replacement for the particular tooth can be made using ceramic material with a ceramic pin so that the entire tooth with the pin may be cured. The pin of the ceramic tooth can then replace the stone model in the tray of the articulator to evaluate its fit in accord with the other teeth of the patient.

As an alternative to a plurality of pins, a spine having a portion that fits into the opening in the tray and a portion which extends above the surface of the tray may be used. When the stone is placed on the tray, it surrounds the spine protruding upward from the tray and, when the stone is removed, the spine may, with the teeth, be separated into segments for further manipulation.

When no spine or pins are to be used, the opening must be broader at the top of the opening (the opening on the superior surface of the tray) with gradual narrowing toward the bottom of the opening. When the tray is formed, the bottom of the opening is sealed so that stone which is forced into the opening can not extrude through the bottom of the opening. When the stone has solidified after taking the reverse impression, the seal is removed and the stone forced out of the opening. The stone forced into the opening on the tray provides stability without use of pins or a spine. However, when no pins or spine are used, a wider opening is needed to accept sufficient stone to stabilize the model. The model can then be cut and reassembled. When no pins or spine are used, it is particularly important that indexing means be provided along the side of the opening.

If the tray is sufficiently thick, the opening may extend only through the tray. However, the tray portion upon which the stone rests may not be of uniform thickness, but may have portions of said tray which extend downward to provide a deeper receptacle for receiving pins, spines or stone.

The articulators of the invention may, alternatively, be made in a horse shoe shape for purposes of making a dental model of both sides of an entire jaw at one time.

Figure 2:
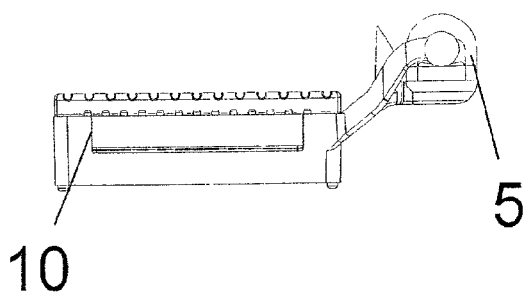
FIG. 2 shows a lateral view of a tray with the hinge part for interaction with a reciprocating hinge part on a second mirror image of said tray.
Figure 3:
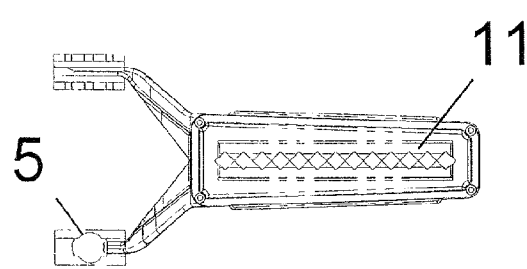
FIG. 3 shows a view of a tray with hinge part from the inferior aspect.
Figure 5:
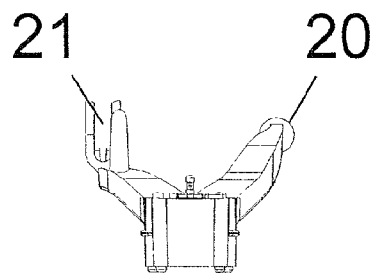
FIG. 5 shows a posterior view of a ball and socket hinge means.

Referring to the drawings, FIG. 1 is a view of the superior surface of the tray (2) for holding stone and the resulting model, said tray having an opening (3) with multiple receptor spaces for receiving indexing pins (4) and having a hinge portion (5) which can interact with reciprocal hinge portions from a second tray. FIG. 2 shows a lateral view of the tray (10) having a hinge part (5). FIG. 3 shows a view of the tray from the inferior aspect (11) with a hinge portion (5), while FIG. 5 shows a hinge portion having a ball (20) and a reciprocating part (21) for accepting a ball from another tray with identical hinge means.

Figure 4:
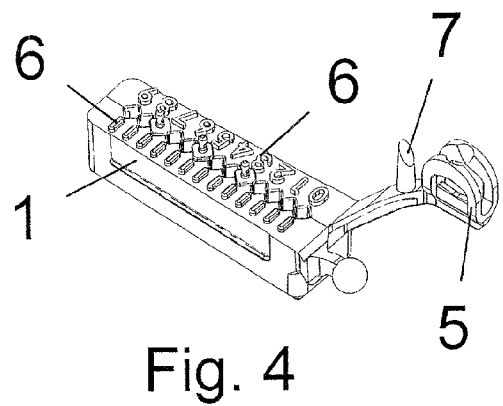
FIG. 4 shows a view of the tray diagonally with views of the side and superior surface of the tray.

FIG. 4 shows a tray (1) with hinge means with a stop (7) and indexing projections on the tray (6) to help hold the stone in place and to act as guides. Indexing means may be any shape, including numbers, which will be useful as guides when replacing portions of the models into the tray. In addition to providing means for indexing, projections of sufficient size (depth) may also provide support and stability to the models on the tray.

Figure 6:
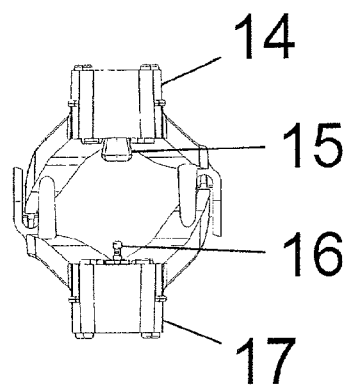
FIG. 6 shows hinges from two trays connected to form completed hinge means.

FIG. 6 shows another view of the hinge means with a stop wherein a spine (15) has been positioned in the upper (maxillary) tray (14) and a pin (16) has been positioned in the lower (mandibular) tray (17).

Figure 7:
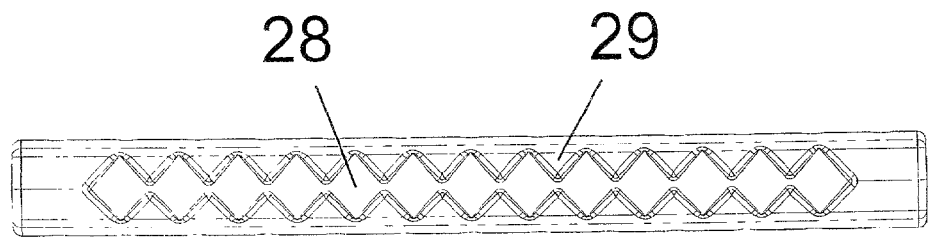
FIG. 7 shows a segment of the opening in the trays for accepting pins indicating one suggested shape of pin-accepting areas.
Figures 8, 9:
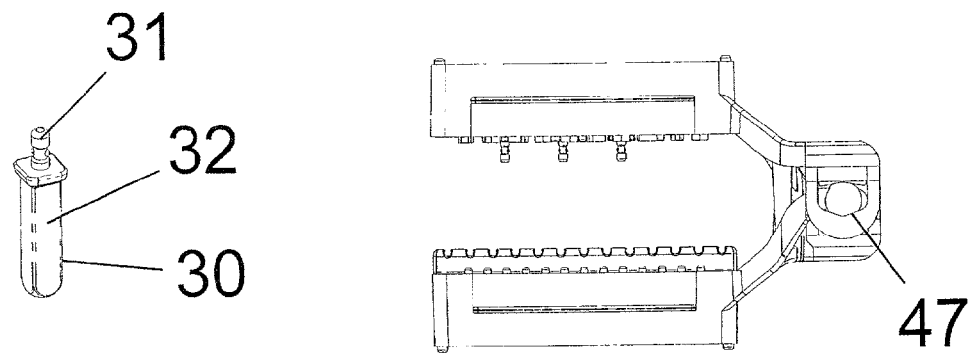
FIG. 8 shows a pin appropriate for insertion into acceptor spaces.
FIG. 9 shows the trays as assembled in interaction with each other when holding mandibular and maxillary models.

FIG. 7 shows an enlargement of a small segment of the tray opening with acceptor spaces (28) and narrowed area (29), said shape being such that the pins remain in one location and one orientation when placed in the tray opening. FIG. 8 shows an indexing pin (30) having a head portion (31) and a base portion (32) which can be placed in the receptor portions of the trays openings.

FIG. 9 shows the trays as arranged in cooperation with each other connected by hinge means when carrying the mandibular and maxillary models. In the instant case, the region of the hinge means which accepts the ball portion of said hinge means (47) is shaped in a "C" to provide ready movement of the ball within the reciprocating part of the hinge.

Figures 10, 11:
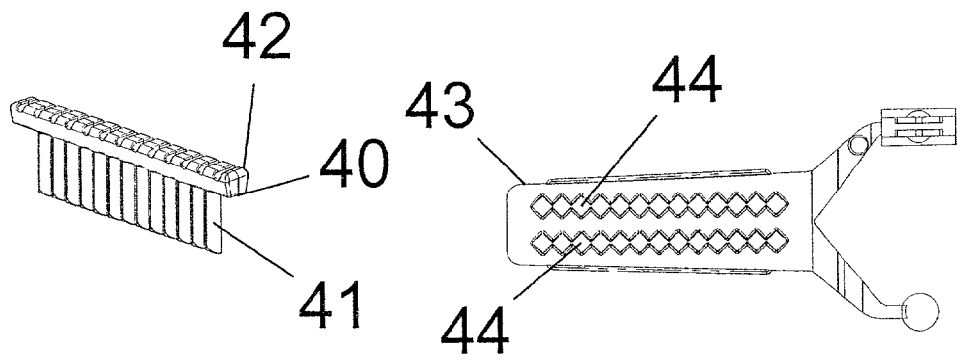
FIG. 10 shows a spine having a portion that can be inserted into the opening of a tray.
FIG. 11 shows a tray having two parallel continuous openings appropriate for receiving pins.

FIG. 10 shows a spine (40) having an insertion portion (41) shaped to fit into an opening in a tray and an upper portion (42) which, when the insertion portion is fitted into the tray opening, rises above the superior surface of the tray. FIG. 11 shows a tray (43) having two openings (44) with multiple receptor spaces. This allows placement of additional pins which may be placed in such a manner that the model of a given tooth has more than one pin.

FIG. 12 shows a tray (50) for use in making a model of all the teeth on one jaw. The tray has projections (51) sufficiently deep to provide stability for the model on the tray. Any projections must, of course, have either straight sides or sides slanted in such a manner that the base (52) is wider than the top (53) (crown) of the projection to ensure that the model may be readily removed from the tray. The projection, on cross section, may be of any shape, including circular, oval, triangular or rectangular. FIG. 13 shows a view of the superior surface of a tray for making a full-jaw model with an opening (54) and projections (55) which are rectangular in cross-section. FIG. 14 shows a spine (56) for use with the tray of FIGS. 12 and 13, having an insertion portion (57) shaped to fit into an opening in a tray and an upper portion (58) which, when the insertion portion is fitted into the tray opening, rises above the superior surface of the tray.

FIG. 15 shows a lateral model of a tray having projections (59) of sufficient depth to provide stability. One advantage in having projections of greater height is that the pins or spine used for insertion into the continuous opening in the tray need not fit so tightly, since the projections upward from the tray provide means of holding the model in place during formation and manipulation of the model. When more loosely fitting spine or pins are inserted into the opening, it is easier to remove the model from the tray.

Figures 16, 17:
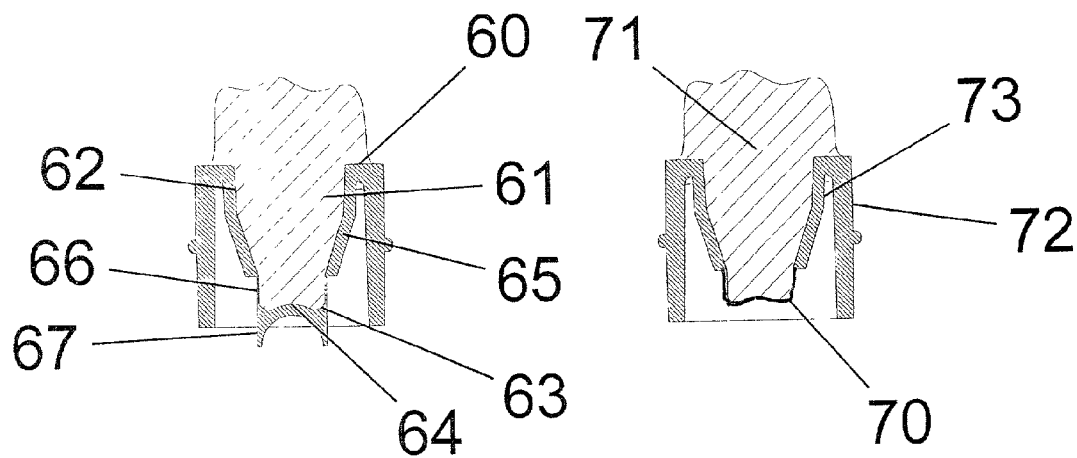
FIG. 16 shows a cross section of the tray transfected at a receptor space which narrows the bottom of the space.
FIG. 17 shows a variation on the tray of FIG. 16 showing a break point on a seal at the bottom of the opening.

FIG. 16 shows a cross section of a plate having a superior surface (60) with the opening (61) being broader at the top (62) and with sides (65) which taper inward at a point nearer the bottom the opening or stone-receiving part (63), said opening having a seal or closure means (64) over the bottom of the opening. This configuration for the opening makes it possible to use the articulator without a spine or pin inserted into any receptor space, since the size of the opening allows sufficient stone to enter the opening to provide stability for the model, and since the tapering of the opening allows the stone to be forced from the opening once the closure means has been removed or loosened. In the particular embodiment of the FIG. 16, the sealing portion covering the bottom of the space is removed when a breakpoint (66) is broken by squeezing projections (67) extending from the bottom of the tray. The model may then be pushed out of the opening through the superior surface of the tray and lifted out of the tray. In FIG. 17, another embodiment, the breakpoint (70) may be positioned on the very bottom of the opening, or (70) may represent a layer of adhesive which holds a sealing strip that can be removed after the stone has dried. This figure also illustrates that the tray need not be of uniform thickness, but may have a portion (73) which extends downward to provide a deepening of the opening (receptor) and a portion (72) that extends downward on the sides of the tray, providing support.

Figure 18:
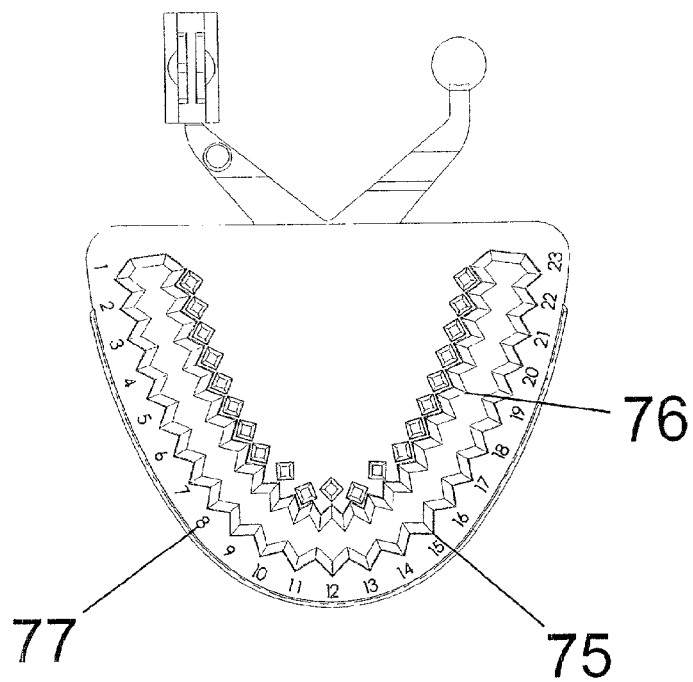
FIG. 18 shows a view from the superior surface of a tray wherein the opening (receptor spaces) in the tray narrow toward the bottom of the receptor space.

FIG. 18 shows a tray for making a model from a full jaw impression wherein said opening, at the superior surface of the tray (75) is broader than the opening at the bottom of the receptor spaces (76). Indexing means (77) using numbers are shown.

The closure means may be any material or configuration that makes it possible to either remove the closure means once the stone has dried or to push the closure means with the stone through the opening and out through the superior surface of the tray. For example, the closure means may be a strip which has been attached adhesively to cover the opening or may be a plate with easily broken areas which allow one to forcibly break the closure means and force the model with parts of the seal out of the opening by exerting pressure on the closure means.

The projections specifically designed and sized to provide greater stability and/or smaller projections which primarily provide indexing means may be in any configuration, and need not be at specific intervals. Factors considered will be the requirement for stability of the model while on the tray and the need for strength of the model when removed from the tray. There may be one or more rows of indexing means, depending on the size and number of continuous openings in the trays, which will affect the space available for indexing means.

I claim:

1. A device comprising:
a first articulator tray having at least one opening with repeating wider and narrower regions which adapted to accept molding material, said tray having a top surface from which said opening extends downward toward a bottom of said tray, wherein said opening to said bottom is closed with a removable seal, said opening having sides, said sides continuously tapering as descending from said top surface so that said opening is wider at said superior top surface, said tray having two extensions which are an integral part of said tray, said extensions being formed as one piece with said tray, wherein one extension has a ball and the other extension has a socket and wherein said ball and said socket together act as reciprocating hinge means parts for interaction with similar extending ball and socket hinge means parts of a second articulator tray.

2. The device of claim 1, wherein the articulator tray has projections on the top surface of said tray.

3. An articulator tray system comprising two identical articulator trays, a first tray and a second tray, each tray having at least one opening which is adapted to accept molding material, each said opening having repeating wider and narrower regions in said at least one opening, each said tray having a top surface from which said opening descends downwards towards a bottom of the tray, said opening continuously tapering as it extends from said top surface, said opening being widest at said top surface of each tray, wherein the opening to said bottom is closed with a removable seal, each said tray also having a two integrally formed extensions from said tray, said extensions being formed as one piece with each said tray, wherein one extension has a ball and the other extension has a socket positioned such that the ball and socket of said first tray interacts reciprocally with ball and socket of said second tray, said interacting balls and sockets thereby forming a hinge means.

* * * * *